United States Patent
Steiness et al.

(10) Patent No.: US 12,083,097 B2
(45) Date of Patent: Sep. 10, 2024

(54) DUAL TNFR1 ANTAGONISTS AND TNER2 AGONISTS FOR USE IN RENAL DISEASES

(71) Applicant: SERODUS AS, Oslo (NO)

(72) Inventors: Eva Steiness, Hellerup (DK); Torben Frank Skarsfeldt, Vedbæk (DK)

(73) Assignee: SERODUS AS, Oslo (NO)

( * ) Notice: Subject to any disclaimer, the term of this patent is extended or adjusted under 35 U.S.C. 154(b) by 0 days.

(21) Appl. No.: 18/252,339

(22) PCT Filed: Nov. 12, 2021

(86) PCT No.: PCT/EP2021/081482
§ 371 (c)(1),
(2) Date: May 9, 2023

(87) PCT Pub. No.: WO2022/101389
PCT Pub. Date: May 19, 2022

(65) Prior Publication Data
US 2023/0414562 A1  Dec. 28, 2023

(30) Foreign Application Priority Data
Nov. 13, 2020  (EP) .................................... 20207534

(51) Int. Cl.
*A61K 31/357* (2006.01)
*A61P 13/12* (2006.01)
(52) U.S. Cl.
CPC ............ *A61K 31/357* (2013.01); *A61P 13/12* (2018.01)
(58) Field of Classification Search
CPC ............................. A61K 31/357; A61P 13/12
See application file for complete search history.

(56) References Cited

U.S. PATENT DOCUMENTS

| 2010/0087517 A1 | 4/2010 | Alberts et al. |
| 2011/0178112 A1 | 7/2011 | Kristiansen et al. |

FOREIGN PATENT DOCUMENTS

| CN | 111825547 A | * 10/2020 | ................ A61P 1/02 |
| WO | 2008/089461 | 7/2008 | |
| WO | WO-2015193630 A1 | * 12/2015 | ......... A61K 31/4365 |

OTHER PUBLICATIONS

CN 111825547A (2020) Specification ProQuest English machine translation Mar. 5, 2024; p. 1-42.*
Steiness Eva et al., "SER150; Low dose anti-thromboxane reduces urinary albumin in patients with Diabetic Kidney Disease", (Oct. 23, 2018), pp. 1-1, URL: https://serodus.com/?mdocs-file=718, (Mar. 15, 2021), XP055795792 [A] 1-6 * the whole document.
Anonymous, "Serodus: Primary endpoint reached by SER150 in a phase 2a study in diabetic nephropathy", Internet Citation, (Mar. 1, 2017), URL: https://www.marketscreener.com/SERODUS-ASA-12957681/news/Serodus- Primary-endpoint-reached-by-SER150-Phase-2a-study-in-Diabetic-Nephropathy-23633713/, (Apr, 21, 2020), XP002798833 [A] 1-6 * the whole document.
Krolewski, A. S., Diabetes Care, (2015), vol. 38, pp. 954-962.
Doody Alison et al, "Validating the association between plasma tumour necrosis factor receptor 1 levels and the presence of renal injury and functional decline in patients with Type 2 diabetes", Journal of Diabetes and Its Complications, (Sep. 18, 2017), vol. 32, No. 1, doi:10.1016/J.JDIACOMP.2017.09.007, ISSN 1056-8727, pp. 95-99, XP085317660 [A] 1-6 * abstract + + p. 98, col. 2, paragraphs 1, 3 *.
Anonymous, "SER150", Internet Citation, (Nov. 16, 2015), URL: https://newdrugapprovals.org/tag/serodus, (Apr. 27, 2020), XP002798834 [A] 1-6 + the whole document *.
Krolewski, A. S. et al., Kidney Int., (Jun. 2017), vol. 91, No. 6, pp. 1300-1311.
Secher T et al., Diabetes, (Jul. 2018), p. 67.
Steiness Eva et al., "SER150: Low dose anti-thromboxane reduces urinary albumin in patients with Diabetic Kidney Disease", (20181023), pp. 1-1, URL: https://serodus.com/?mdocs-file=718, (20210415), XP055795792 [A] 1-6 * the whole document.

* cited by examiner

*Primary Examiner* — John M Mauro
(74) *Attorney, Agent, or Firm* — DUANE MORRIS LLP; Gregory M. Lefkowitz; Brandon A. Chan (57) ABSTRACT

The present invention relates to certain 2,4-diphenyl-1,3-dioxanes that are capable of reducing Tumor necrosis factor receptor 1 (sTNFR1) and capable of increasing Tumor necrosis factor receptor 2 (sTNFR2) and their use in the treatment of specific subpopulations with a renal disease such as diabetic nephropathy.

9 Claims, 4 Drawing Sheets

DUAL TNFR1 ANTAGONISTS AND TNER2 AGONISTS FOR USE IN RENAL DISEASES

CROSS-REFERENCE TO RELATED APPLICATIONS

This application is a § 371 national stage entry of International Application No. PCT/EP2021/081482, filed Nov. 12, 2021, which claims priority to European Application No. 20207534.7, filed Nov. 13, 2020, the entire contents of which are incorporated herein by reference.

TECHNICAL FIELD

The present invention relates to the finding that certain 2,4-diphenyl-1,3-dioxanes are capable of reducing Tumor necrosis factor receptor 1 (sTNFR1) and capable of increasing Tumor necrosis factor receptor 2 (sTNFR2). Thus, the mixed profile of reducing sTNFR1 and increasing sTNFR2 makes such compounds promising drug candidates for use in the treatment of renal diseases, in particular in the treatment of certain patient sub-populations suffering from a renal disease, wherein the pro-inflammatory pathway of TNFR1 is highly elevated. Thus, the present invention relates to certain 2,4-diphenyl-1,3-dioxanes for use in the treatment of a renal disease, in particular diabetic nephropathy, in a sub-population of patients characterized by having a serum level of sTNF1R >2.9 ng/mL and/or ACR >300 mg/g.

BACKGROUND OF THE INVENTION

Diabetic nephropathy is a medical term used to denote diseases or damages of the kidney in diabetic patients, which eventually leads to chronic kidney disease (CKD). It is a progressive disease and is more common in people who have had either type 1 or type 2 diabetes for a long time period, such as 10-20 years or more. Diabetic nephropathy is relatively common, and it is estimated that around 40 percent of people who have type 1 or 2 diabetes develop some stage of CKD. Furthermore, as of 2019, the International Diabetes Federation estimated that 463 million people worldwide are suffering from diabetes. CKD can be classified into five stages, where stage 5 (kidney failure or end-stage renal disease (ESRD)) is the last, which is when the patient will require regular dialysis or kidney transplantation. The stages are determined by the extent of the kidney damage and the glomerular filtration rate (GFR). Signs of kidney damage can be seen in blood, urine, in kidney biopsies or by imaging studies and include the measurement of albumin/creatinine ratio (ACR). Stage 1: Kidney damage is present but with normal or relatively high kidney function with GFR above 90, Stage 2: Kidney damage is present with some loss of kidney function; GFR between 60 and 89, Stage 3: Mild to severe loss of kidney function; GFR between 30 and 59, Stage 4: Severe loss of kidney function; GFR between 15 and 29 and Stage 5: Kidney failure; GFR less than 15.

According to a recent U.S. Report (U.S. Renal Data System Annual Data Report 2019, Centers for Medicare & Medicaid Services), 124,500 new cases of ESRD were registered in 2017, and more than 746,557 Americans were being treated for ESRD, wherein around 39% of the cases resulted from diabetic nephropathy. The costs of treatment are staggering: In 2017, hemodialysis treatment cost an average of $91,795 per patient annually in the United States, which amounted to a total annual hemodialysis cost in the United States of around $28 billion; In 2017, the total Medicare spending on both CKD and ESRD patients was in excess of $120 billion. Apart from the huge economic costs to the society, patients affected with CKD or ESRD are also personally seriously hampered in their daily life and often have great difficulties maintaining ordinary jobs, as their disease requires severe diet restrictions and at the end very frequent dialysis. Usually, each dialysis treatment lasts about four hours, and is done three times per week.

CKD may result from different kidney diseases, such as diabetic nephropathy, glomerulonephritis, glomerulosclerosis or hypertensive nephrosclerosis despite the fact that the etiology and pathology behind the kidney diseases differ. Glomerulonephritis refers to inflammation in the glomeruli (the small capillaries in the kidney surrounded by Bowman's capsule) and may be caused by autoimmune response or infections and typically results in one or both nephrotic or nephritic syndromes. Glomerulosclerosis refers to scarring or hardening of the glomeruli and may arise from different etiology, such as morbid obesity, HIV infection, birth defects, drug abuse or genetic causes. Hypertensive nephrosclerosis refers to damage to the kidney due to chronic high blood pressure causing hyperfiltration resulting in hardening and thickening of the kidney tissue including the glomeruli, kidney tubules and interstitial tissues. Diabetic nephropathy refers to damage to the kidneys in patients suffering from diabetes. The pathophysiology of diabetic nephropathy is thought to involve an interaction between hemodynamic and metabolic factors. Hemodynamic factors include an increase in systemic and intraglomerular pressure as well as the overactivation of the renin-angiotensin-aldosterone system (RAAS). Due to the higher load of filtered glucose in diabetic patients with poor control of blood sugar, there is an up-regulation in the sodium-glucose cotransporter 2 (SGLT2) in the proximal tubules, which cotransports sodium and glucose back into circulation. This leads to a decrease in the delivery of sodium chloride to the macula densa in the distal tubules. The macula densa cells sense the change in sodium chloride levels and trigger an autoregulatory response by releasing renin and overactivating RAAS, thereby increasing blood pressure. Furthermore, metabolic factors include the formation of advanced glycation end products (AGEs) due to the higher blood sugar concentration in diabetic patients with poor control of blood glucose. The AGE products formed activate RAGE receptors, which is a signal transduction receptor found on a number of cell types including macrophages, endothelial cells, renal mesangial cells and podocytes in the glomerulus. Activation of RAGE receptors enhances the production of cytosolic Reactive Oxygen Species (ROS) as well as stimulates intracellular molecules, such as nuclear factor kappa B (NF-kB). These factors lead to podocyte injury, oxidative stress, inflammation, and fibrosis and in turn decreased kidney function. Diabetic nephropathy usually accompanies albuminuria with glomerular hyperfiltration and renal hypertrophy in the early stage, followed by an increased urinary content of albumin and a gradual decrease in GFR, often showing a deteriorating course that will lead to ESRD. Current treatments for diabetic nephropathy include angiotensin-converting enzyme (ACE) inhibitors to lower blood pressure, hypoglycaemic drugs to keep a stringent control of blood glucose, as well as lifestyle measures including exercise and healthy diet. Recently, treatment with empagliflozin (a sodium-dependent glucose transporter 2 inhibitor) has also shown to stabilize renal function.

Currently, two tests are used to diagnose CKD: creatinine-based eGFR (estimated GFR) and ACR (Albumin-to-creatinine ratio). The glomerular filtration rate (GFR) describes the volume of fluid filtered per unit time in the kidney from the glomerular capillaries into the Bowman's capsule. Creatinine clearance is the volume of blood plasma that is cleared of creatinine per unit time and is a useful measure for approximating the GFR, as creatinine is freely filtered through the glomeruli and not reabsorbed from the tubules. ACR is a measure of the albumin-to-creatinine ratio in urine. Albumin is one of the first proteins to be detected in the urine of patients with kidney damage and also constitutes the largest proportion of the excreted proteins. Albumin is a plasma protein that is present in high concentrations in the blood, and when the kidneys are functioning properly, virtually no albumin is present in the urine. If a person's kidneys become damaged or diseased, however, they may often lose their ability to conserve albumin and other proteins.

Patients diagnosed with diabetic nephropathy have a progressive renal decline. It progresses at an almost steady, linear rate until ESRD is reached, albeit at widely differing rates among individuals. The currently employed diagnostic methods mentioned above, ACR and creatinine-based eGFR, cannot reliably distinguish which declines will be "very fast", "fast", "moderate", or "slow". Thus, increase in urinary albumin excretion is an important determinant of diabetic nephropathy disease progression, but it does not entirely explain the phenomenon of why some patient groups have a more rapid progressive renal decline compared to other patient groups, despite initially having similar ACR and/or eGFR values.

The tumor necrosis factor receptor superfamily (TNFRSF) is a protein superfamily of cytokine receptors characterized by the ability to bind tumor necrosis factors (TNFs) via an extracellular cysteine-rich domain. The family comprises tumor necrosis factor receptor 1 (TNFR1) and tumor necrosis factor receptor 2 (TNFR2) among other receptors. TNFR1 and TNFR2 exist both as membrane bound receptors (mTNFR1 and mTNFR2) and as soluble forms (sTNFR1 and sTNFR2) and are activated by binding of the proinflammatory cytokine TNF-α, which is involved in systemic inflammation. Hence, levels of TNFR1/2 measured in serum or urine is the soluble forms (sTNFR1 and sTNFR2). TNF-α also exists in both a soluble form (sTNF-α) and a membrane bound form (mTNF-α). Evidence has demonstrated that mTNFR1 is ubiquitously expressed on almost all cells, while mTNFR2 exhibits a more limited expression, predominantly on regulatory T cells (Tregs). The TNFRs have different affinities for the soluble TNF-α (sTNF-α) and the membrane-bound TNF-α (mTNF-α). TNFR1 binds both forms equally well, whereas TNFR2 has a higher affinity for the membrane-bound form.

Within recent years, a new model of diabetic nephropathy in type 1 and type 2 diabetes has been proposed by A. Krolewski and his coworkers (*Diabetes Care* 2015; 38:954-962 and *Kidney Int* 2017 June; 91(6): 1300-1311) by which the predominant clinical feature of both early and late stages of diabetic nephropathy is the rate of progressive renal decline (eGFR slope measured in mL/min/1.73 m²/year). Krolewski et al. found that while an individual's rate of renal decline is constant, the eGFR slope varies widely among individuals from −72 to −3.0 ml/min/1.73 m²/year, depending on the serum levels of sTNFR1, even if the individuals initially had similar ACR and/or GFR values. Krolewski et al. partitioned the patients into "very fast", "fast", "moderate" and "slow" decliners and demonstrated that "fast" and "very fast" decliners declined from normal eGFR to ESRD within 2-10 years (see FIG. 1). It was found that the highest cumulative risk of ESRD within the 3-year follow-up was for patients with baseline serum sTNFR1 >4.3 ng/ml regardless of the values of other markers such as ACR and GFR. The results are summarized in FIG. 1. The high-risk group of patients with diabetic nephropathy (the "fast" renal decliner group) is thus distinguished from other patient groups with diabetic nephropathy (such as the "moderate" or "slow" decliners), whose renal decline progress more slowly. These patient groups—the fast and moderate decliners—thus constitute separate groups of patients characterized by their specific physiological and/or pathological status of having increased sTNF1R values in serum. The finding that elevated serum sTNFR1 determines the rate of progressive renal decline suggests that the proinflammatory pathway of TNF1R plays a crucial role and that new treatments should at least aim at antagonizing/reducing TNFR1 in order to slow the progression of the disease.

Recent findings point to the importance of the soluble circulating levels of the sTNFR1 and sTNFR2 rather than the cellular signal transduction through the membrane bound receptors mTNFR1 and mTNFR2. However, the regulation mechanisms of sTNFR have not yet been fully understood. Some studies have suggested that TNF-α is the main regulator, as this cytokine induces shedding of the TNFRs from the membrane. Also in urine, increased sTNFRs excretion reflects increased shedding of TNFRs from the cell membranes which may be interpreted as a marker of increased TNF-α expression in activated renal cells. It has further been shown that there is a strong correlation between sTNFRs in serum and sTNFRs in urine. Thus, high levels of sTNFRs in serum correspond to high levels of sTNFRs in urine and vice versa. Although the exact physiological role of sTNFRs remains unknown, the specific involvement of the TNFR-mediated pathways, rather than a general inflammation, in the development of early and late loss of renal function in both type I and type II diabetes has been recently suggested.

It is known that binding of sTNF-α via TNFR1 mainly triggers pro-inflammatory pathways, whereas mTNF-α binding via TNFR2 triggers immune modulation and tissue regeneration. Thus, a promising therapeutic strategy for the treatment of inflammatory diseases would be to selectively block the sTNF-α/TNFR1 pathway through the administration of sTNF-α inhibitors/scavengers, TNFR1 antagonists or by reducing the serum levels of sTNFR1 while keeping the TNFR2 signaling pathway intact. Another promising strategy would be to rely on TNFR2 agonists or by increasing the serum levels of sTNFR2, which could drive the expansion of regulatory T cells and promote tissue regeneration. Thus, future treatments of renal diseases, such as diabetic nephropathy, should aim at identifying molecules capable of modulating TNFRs by decreasing or antagonizing TNFR1 and increasing or agonizing TNFR2. Currently, to the best of the applicant's knowledge, there is no known molecules that act by decreasing or antagonizing TNFR1 and at the same time act by increasing or agonizing TNFR2. Thus, there is an unmet need in the art of finding new therapies capable of decreasing or antagonizing TNFR1 and increasing or agonizing TNF2R, thereby decreasing sTNF1R pathway and increasing sTNFR2 pathway. In particular, such compounds would be valuable to treat certain subpopulations of subjects characterized in having highly elevated TNFR1 and suffering from renal diseases, in particular diabetic nephropathy, before their nephropathy develops irreversibly into ESRD in the course of a few years.

SUMMARY OF THE INVENTION

The present inventors have discovered that (Z)-6-((2S,4S,5R)-2-(2-chlorophenyl)-4-(2-hydroxyphenyl)-1,3-dioxancis-5-yl) hex-4-enoic acid or a pharmaceutically acceptable salt thereof acts by reducing or antagonizing Tumor necrosis factor receptor 1 (TNFR1) and by increasing or agonizing Tumor necrosis factor receptor 2 (TNFR2). Thus, the inventors have demonstrated that the compound of the invention is capable of decreasing sTNFR1 and at the same time increasing sTNFR2 in an animal model of diabetic nephropathy compared to placebo treated rats, thereby decreasing the proinflammatory pathways of TNFR1 and increasing the tissue regeneration mediated pathways of TNFR2. Therefore, the compound according to the invention is more useful in the treatment of renal diseases, in particular diabetic nephropathy, in the patient sub-groups characterized by having an elevated level of sTNFR1 compared to other patient sub-groups where the TNFR1 pathway is less pronounced. Further, it was surprisingly found that better treatment effect was observed in patients having an ACR >300 mg/kg.

Thus, in a first aspect the invention thus relates to a compound of Formula (I) or a pharmaceutically acceptable salt thereof:

Formula (I)

for use in the treatment of a renal disease in a group of patients characterized by having a serum sTNFR1 value >2.9 ng/mL and/or an ACR >300 mg/g.

DEFINITIONS

In the present context, the term "treatment" should be understood in the broadest sense as prevention, amelioration, or treatment. Thus, treatment is also intended to include prophylactic treatment. Therefore, treatment of a renal disease may refer to the prevention or retarding of the loss of kidney function or partially reverse the loss of kidney function as estimated by ACR and/or eGFR.

In the present context, the term "pharmaceutical acceptable salts" refers to all type of salts that are used in pharmaceuticals to convert an acid into a salt. The salt may be formed by an addition of a base to the compound of Formula (I). Typical examples can be found in the Handbook of Pharmaceutical Salts: Properties, Selection, and Use, 2nd Revised Edition P. Heinrich Stahl (Editor), Camille G. Wermuth (Editor) ISBN: 978-3-906-39051-2 Apr. 2011, 388 Pages.

In the present context, "sTNFR1" refers to the soluble TNF Receptor type 1. The sTNFR1 can be measured in either serum or urine according to the procedures described herein.

In the present context, "sTNFR2" refers to the soluble TNF Receptor type 2. The sTNFR2 can be measured in either serum or urine according to the procedures described herein.

According to the present invention, sTNFR1 and sTNFR2 are measured in serum or urine according to the procedures described in Krolewski A. S. *Diabetes Care* 2015; 38:954-962 and Krolewski A. S. et al. *Kidney Int* 2017 June; 91(6): 1300-1311. Briefly, all markers were measured by immunoassay. Samples were thawed, vortexed, and centrifuged, and measurements were performed in the supernatant. sTNFR1 and sTNFR2 were measured by ELISA (DRT100, DRT200, and high-sensitive immunoassay HS600B, respectively; R&D, Minneapolis, Minnesota) according to the manufacturer's protocol.

Other definitions as used herein are as follows:
ACR: Albumin-to-creatinine ratio
eGFR: estimated GFR
ESRD: end-stage renal disease
GFR: glomerular filtration rate
NA: normoalbuminuria
MA: microalbuminuria
T1DM or T1D: diabetes (mellitus) type 1
T2DM or T2D: diabetes (mellitus) type 2

DETAILED DESCRIPTION OF THE INVENTION

The present invention relates to (Z)-6-((2S,4S,5R)-2-(2-chlorophenyl)-4-(2-hydroxyphenyl)-1,3-dioxan-cis-5-yl) hex-4-enoic acid or a pharmaceutically acceptable salt thereof for use in the treatment of renal diseases, in particular diabetic nephropathy. This compound belongs to a class of 2,4-diphenyl-1,3-dioxanes which have previously been shown to be thromboxane receptor antagonists, thromboxane synthase inhibitors and/or PPAR agonists. Thus, this class of compounds has previously been shown to have an effect on glucose uptake (see e.g. example 28, in WO 2007/138485), antagonize the thromboxane receptor (see e.g. example 29, in WO 2007/138485) and inhibit cell proliferation (see e.g. example 30, in WO 2007/138485). Thus, previously published data have supported that this class of compounds could have potential as antihyperglycemic agents, anticancer agents and/or anticoagulants.

The present inventors have now surprisingly found that (Z)-6-((2S,4S,5R)-2-(2-chlorophenyl)-4-(2-hydroxyphenyl)-1,3-dioxan-cis-5-yl) hex-4-enoic acid or a pharmaceutically acceptable salt thereof also reduces the serum or urine level of/acts as an antagonist of Tumor necrosis factor receptor 1 (TNFR1) and increases the serum and urine level of/acts as an agonist at Tumor necrosis factor receptor 2 (TNFR2). This finding makes the compound of the invention useful in the treatment of renal diseases, in particular diabetic nephropathy, more particularly the treatment of renal diseases in the subgroups of patients with renal diseases characterized by having an elevated sTNFR1 level in serum or urine.

Figure 2:
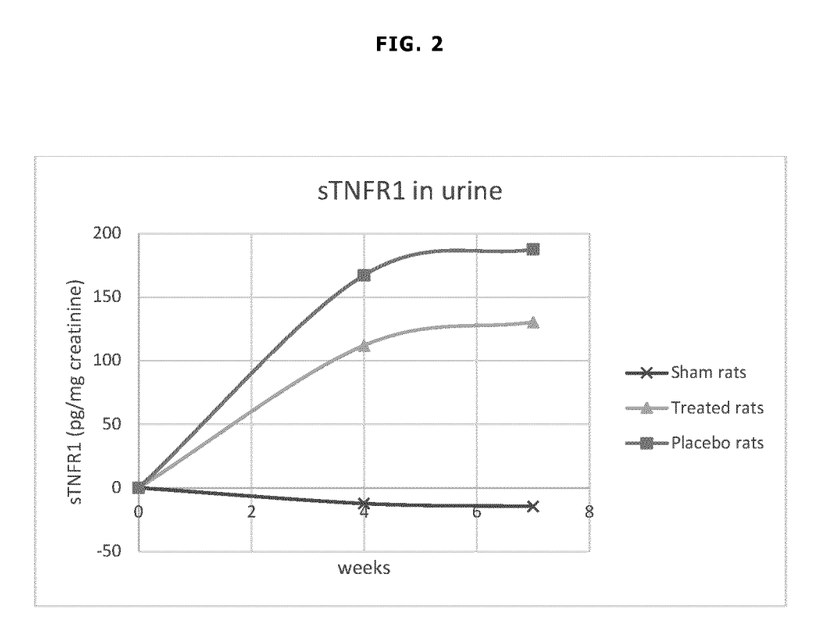
FIG. 2 shows the measurement of urine TNFR1-to-creatinine changes (pg/mg) from baseline value and after 4 and 7 weeks in Sham-operated rats and Px-UNx operated rats receiving placebo or treatment with compound 1. The data for the doses 1, 3 and mg/kg, p.o. was pooled. Values represent mean±SEM. The figure shows that Sham-operated rats experience a slight reduction in TNFR1 levels over the 7 weeks of the study, whereas the Px-UNx operated rats receiving placebo (vehicle) display rapidly increasing levels of TNFR1 over the same period. The compound 1 treated, Px-UNx operated rats also display increasing levels of TNFR1 over the 7-week period, but significantly less than for the placebo control group.
Figure 3:
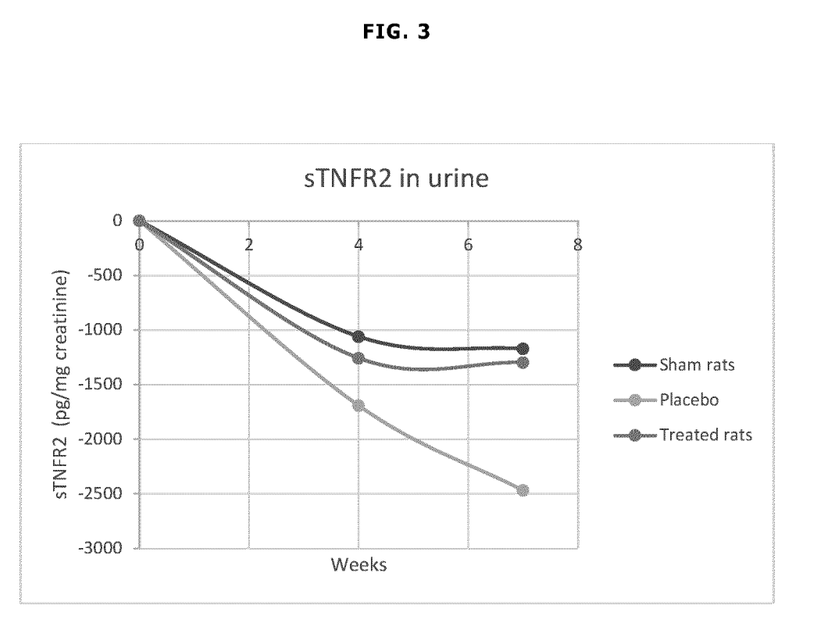
FIG. 3 shows the measurement of urine TNFR2-to-creatinine changes (pg/mg) from baseline value after 4 and 7 weeks in Sham-operated rats and Px-UNx operated rats receiving placebo or treatment with compound 1 (3 mg/kg, p.o.). Values represent mean±SEM. The figure shows that Sham-operated rats experience a slight reduction in TNFR2 levels over the 7 weeks of the study, whereas the Px-UNx operated rats receiving placebo (vehicle) display rapidly decreasing levels of TNFR2 over the same period. The compound 1 treated, Px-UNx operated rats show decreasing levels of TNFR2 but much less compared to the placebo control group.

The inventors surprisingly found that compound 1 is capable of decreasing the level of sTNFR1 in Px-UNx operated rats compared to Px-UNx operated rats receiving placebo (see FIG. 2). Furthermore, the inventors surprisingly found that compound 1 is capable of increasing the level of sTNFR2 in Px-UNx operated rats compared to Px-UNx operated rats receiving placebo (see FIG. 3). This finding was surprising, since compound 1 as a thromboxane receptor antagonist, thromboxane synthase inhibitor and PPAR agonist was not expected to modulate the level of TNFR1, since no biological link exists between these receptors and TNFR1. Thus, these new findings have resulted in a new clinical use, namely the use for the treatment of certain sub-groups suffering from a renal disease and characterized in having and elevated sTNFR1 and/or a decreased sTNFR2 and thereby the fastest decline in renal function.

Thus, in a first aspect the invention relates to a compound of formula (I) or a pharmaceutically acceptable salt thereof, formula (I)

for use in the treatment of a renal disease in a group of patients characterized by having a serum level of sTNFR1 of >2.9 ng/mL and/or an ACR >300 mg/g.

Renal Diseases

In an embodiment of the invention, the renal disease is selected from group consisting of diabetic nephropathy, glomerulonephritis, glomerulosclerosis or hypertensive nephrosclerosis. In the most preferred embodiment, the renal disease is diabetic nephropathy.

Patient Groups

As mentioned above, patients suffering from a specific renal disease cannot be considered a single uniform group but can be further divided into sub-groups based on e.g. the levels of sTNFR1. As exemplified in FIG. 1, patients suffering from diabetic nephropathy can be further classified as either "fast decliners", "moderate decliners" or "slow decliners", depending on the rate at which the renal function declines (slope of eGFR). Thus, subjects that are initially classified with the same stage (1-5) of diabetic nephropathy, due to similar ACR and GFR values, may have completely different progression of the disease due to highly different rates in their renal function decline. The rate at which renal function declines is determined by the serum or urine levels of sTNFR1 emphasizing the role of sTNFR1 and its pro-inflammatory signaling pathways in the rate of disease progression. According to Krolewski et al., the "fast decliners" reach ERSD within approximately 2-10 years and were characterized in having a serum of TNFR1 >4.3 ng/mL. The "moderate decliners" reach the ERSD within approximately years and are characterized in having a TNFR1 2.9-4.3 ng/mL. Finally, the slow decliners reach the ERSD within 20-45 years and are characterized in having a serum level of TNFR1<2.9 ng/mL (see FIG. 4). The compound according to the invention or a pharmaceutically acceptable salt thereof is therefore particularly useful in the treatment of the sub-groups characterized in having serum levels of sTNFR1 >2.9 ng/mL, such as a sTNFR1 value between 2.9-4.3 ng/mL, most preferably serum level of sTNFR1 >4.3 ng/mL. Thus, the compounds according to the invention are particularly useful in slowing the progression of diabetic nephropathy in the groups that have a high risk of developing ESRD or losing 40% of baseline eGFR in the course of a few years, as the high levels sTNFR1 cause the rapid disease progression. Therefore, in a preferred embodiment, the treatment is for use in a sub-group of patients suffering from a renal disease characterized by having a serum level of sTNFR1 >2.9 ng/mL (i.e. a "moderate decliner" or a "fast decliner"). In a preferred embodiment, the treatment is for use in a sub-group of patients suffering from a renal disease characterized by having a serum level of sTNFR1 value between 2.9-4.3 ng/mL (i.e. a "moderate decliner"). In a more preferred embodiment, the treatment is for use in the subpopulation of human subjects suffering from a renal disease characterized by having a serum level of sTNFR1 >4.3 ng/mL (i.e. a "fast decliner"). In particular, the invention is useful for the treatment of diabetic nephropathy. Thus, in an even more preferred embodiment, the treatment is for use in the sub-group of patients suffering from diabetic nephropathy characterized by having a serum level of sTNFR1 between 2.9-4.3 ng/mL (i.e. a "moderate decliner"). In the most preferred embodiment, the treatment is for use in the sub-group of patients suffering from diabetic nephropathy characterized by having a serum level of sTNFR1 >4.3 ng/mL (i.e. a "fast decliner"). As mentioned above, diabetic nephropathy may occur as a long-term complication of both type 1 diabetes and type 2 diabetes. Thus, in a particular embodiment, the clinical condition is diabetic nephropathy as a long-term complication of type 1 diabetes. In yet another particular embodiment, the clinical condition is diabetic nephropathy as a long-term complication of type 2 diabetes.

Figure 1:
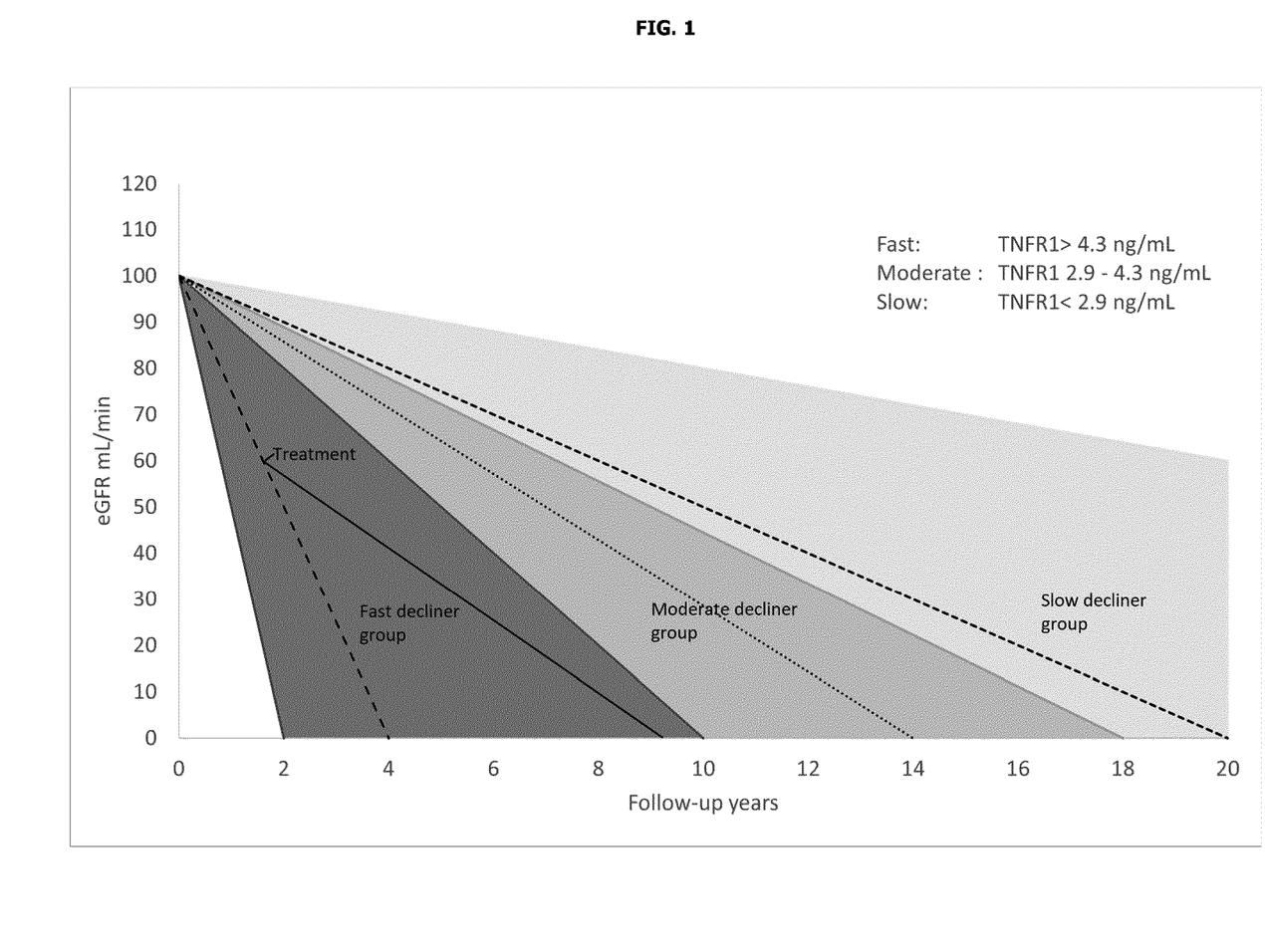
FIG. 1 shows a schematic representation of an eGFR trajectory in the fast decliner group (TNFR1>4.3 ng/mL), an eGFR trajectory in the moderate decliner group (TNFR1 2.9-4.3 ng/mL) and an eGFR trajectory in the slow decliner group (TNFR1<2.9 ng/mL) that are untreated (dashed lines). When lowering the TNFR1 values by treatment (black solid line), the eGFR slope is changed such that ESRD is postponed. (Figure adapted from A. Krolewski et al., Kidney Int. 2017 June; 91(6): 1300-1311).

When lowering the TNFR1 values, the slope of eGFR is decreased such that the onset of ESRD is postponed. FIG. 1 illustrates an eGFR slope of a patient in the "fast decliner sub-group" (dashed line) that is shifted into an eGFR slope corresponding to the eGFR slopes in the "moderate decliner sub-group" (solid line), thereby postponing the onset of ESRD by approximately 5 years. It follows that the treatment of the renal diseases should preferably be started as early as possible in order to obtain the best clinical outcome. Thus, in an embodiment of the invention, the treatment is for use in the sub-group of patients suffering from a renal disease and having kidney failure (stage 5 with GFR less than 15) and a serum level of sTNFR1 >2.9 ng/mL, most preferably >4.3 ng/mL. In a preferred embodiment, the treatment is for use in the sub-group of human subjects suffering from a renal disease and having severe loss of kidney function (stage 4 with GFR less between 15 and 29) and a serum level of sTNFR1 >2.9 ng/mL, most preferably >4.3 ng/mL. In a more preferred embodiment, the treatment is for use in the sub-group of patients suffering from a renal disease and having mild to severe loss of kidney function (stage 3 with GFR less between 30 and 59) and a serum level of sTNFR1 >2.9 ng/mL, most preferably >4.3 ng/mL. In a yet more preferred embodiment, the treatment is for use in the sub-group of patients suffering from a renal disease and having kidney damage with some loss of kidney function (stage 2 with GFR less between 60 and 89) and a serum level of sTNFR1 >2.9 ng/mL, most preferably >4.3 ng/mL. In the most preferred embodiment, the treatment is for use in the sub-group of patients suffering from a renal disease and having kidney damage present but a normal kidney function (stage 1 with GFR above 90) and a serum level of sTNFR1 >2.9 ng/mL, most preferably >4.3 ng/mL. In any of the above embodiments, the renal disease is preferably selected as diabetic nephropathy.

In another highly preferred embodiment, the compound of formula (I) is for use in the treatment of diabetic nephropathy in the sub-group of patients characterized by having a normal glomerular filtration rate (GFR) of above 90 mL/min, an ACR >1.9 g albumin/g creatinine in urine and a serum level of sTNFR1 >2.9 ng/mL, most preferably >4.3 ng/mL.

In another highly preferred embodiment, the compound of formula (I) is for use in the treatment of diabetic nephropathy in the sub-group of patients characterized by having a normal glomerular filtration rate (GFR) of above 90 mL/min, an ACR >300 mg albumin/g creatinine in urine and a serum level of sTNFR1 >2.9 ng/mL, most preferably >4.3 ng/mL.

Doses

The inventors initially tested compound 1 in a surgery-induced animal (rat) model of Diabetic Nephropathy (Secher T et al. *Diabetes* 2018 July; 67(Supplement 1)). In this model, elevated levels of circulating TNFR1 can be observed in the urine in the "fast decliners" similarly to the findings of Krolewski et al. In the rat study, the inventors surprisingly found a reduction of the levels of TNFR1 by compound 1 compared to placebo treatment over the full treatment period of 7 weeks (see FIG. 2).

Three active doses of 1, 3 and 10 mg/kg of compound 1 were administered orally once daily to 90% pancreatectomized and uninephrectomized rats over 49 days. A control group received placebo, and another control group underwent surgery to mimic the 90% pancreatectomy (Px) and uninephrectomy (UNx) without affecting the function of the kidney or the pancreas (Sham model). The Sham group also received placebo. The conclusion from the rat study was that compound 1 reduced the level of sTNFR1 in the urine over the full treatment period (see FIG. 2). As can be seen from FIG. 2, Sham-operated rats experience a slight reduction in sTNFR1 levels over the 7 weeks of the study, whereas the Px-UNx operated rats receiving placebo (vehicle) display rapidly increasing levels of sTNFR1 over the same period. The compound 1 treated and Px-UNx operated rats also display increasing levels of TNFR1 over the 7-week period, but significantly less than for the placebo control group. The daily doses in the rat model may be converted into equivalent doses in humans (Guidance for Industry: Estimating the Maximum Safe Starting Dose in Initial Clinical Trials for Therapeutics in Adult Healthy Volunteers, 2005). Thus, the 1 mg/kg daily dose corresponds to a human daily dose of 0.16 mg/kg or 11.2 mg for a 70-kg patient. Likewise, a 3 mg/kg daily dose corresponds to a human daily dose of 0.48 mg/kg or 33.6 mg for a 70-kg patient. Finally, a 10 mg/kg daily dose corresponds to a human daily dose of 1.6 mg/kg or 112.7 mg for a 70-kg patient. As seen in Example 1, no statistically significant difference between dosage levels (1, 3 or 10 mg) could be observed. This suggests that full efficacy is already obtained at the lowest dose and hence that even lower daily doses than 1 mg/kg are enough to lower the sTNFR1 in urine in the animal model.

Thus, based on the animal study and applying the above-mentioned dose conversion to human doses, equivalently therapeutically effective daily doses were shown to lie in the range of 0.16 mg/kg-to 1.6 mg/kg. However, since all doses were found to be equally effective, the data from the animal model suggests that even lower daily doses than 0.16 mg/kg of compound 1 are effective in decreasing the sTNFR1. This effectively means that sTNFR1 may be reduced in a patient with minimal effect on the coagulation system (through antagonizing the thromboxane receptor or thromboxane synthetase) where higher doses are needed.

Thus, in a preferred embodiment, the compound of formula (I) or a pharmaceutically acceptable salt thereof is administered to a patient in a therapeutically effective dose corresponding to a daily dose of <1.6 mg/kg, preferably less than 0.48 mg/kg, even more preferably less than 0.16 mg/kg, such as a daily dose in the range of 0.01-1.6 mg/kg, more preferably 0.05-0.48 mg/kg more preferably 0.1-0.16 mg/kg. In another embodiment of the invention, the compound of formula (I) or a pharmaceutically acceptable salt thereof is administered to a patient as a daily dose in the range of 0.16 mg/kg to 1.6 mg/kg. In another preferred embodiment of the invention, the compound of formula (I) or a pharmaceutically acceptable salt thereof is administered to a patient as a daily dose in the range at 0.3 mg/kg to 0.625 mg/kg. In yet another embodiment of the invention, the compound of formula (I) or a pharmaceutically acceptable salt thereof is administered to a patient as a daily dose at 0.3 mg/kg or 0.625 mg/kg.

Dosing Regimen

The dosing regimen may include a single daily dose as described herein or be divided into multiple smaller daily doses such that an effective therapeutic plasma concentration of the drug is reached. The benefit of multiple smaller doses is less fluctuations in the plasma drug concentration which may be necessary for drugs having a narrow therapeutic window or a short half-life. The drawback of more complex dosing regimens may be less optimal patient compliance. In an embodiment, the dosing regimen comprises a single daily dose as described herein. In another embodiment, the dosing regimen comprises two daily doses wherein each dose is half the size of the single daily dose. Preferably, for patient compliance reasons, single daily doses are preferred.

Thus, in an embodiment of the invention, there is provided a compound of Formula (I) or a pharmaceutically acceptable salt thereof for use in the treatment of a population of patients with diabetic nephropathy characterized by having a serum level of sTNFR1 >2.9 ng/mL, most preferably >4.3 ng/mL, wherein said patient receives a daily dose as described above under the section "Doses" for as long as treatment is required (i.e. as long as elevated sTNFR1 levels are present in urine or serum). Due to the progressive nature of loss of kidney function as described above, the treatment period may in some embodiments last for several weeks, months or years, most preferably the treatment is a chronic treatment.

The compound of Formula (I) or a pharmaceutically acceptable salt thereof may be administered together with one or more additional medicaments used in the treatment of diabetic nephropathy, such as angiotensin-converting enzyme (ACE) inhibitors or hypoglycaemic drugs.

Pharmaceutical Acceptable Salts

The compound of formula (I) may be used either as the free carboxylic acid or a pharmaceutical acceptable base addition salt thereof. Salt formation is a well-known and effective method in improving solubility and dissolution rate of both acidic and basic drugs. Thus, in a preferred embodiment the compound of formula (I) is a salt. Suitable salts include, but are not limited to, salts comprising alkali metals or alkaline earth metals, such as the sodium salt, potassium salt or calcium salt of the compound of formula (I). Other salts may include suitable ammonium salts formed by reacting the acid of formula (I) with an appropriate amine. Examples of suitable salts can be found in the Handbook of Pharmaceutical Salts: Properties, Selection, and Use, 2nd Revised Edition P. Heinrich Stahl (Editor), Camille G. Wermuth (Editor) ISBN: 978-3-906-39051-2 Apr. 2011 388 Pages. In the most preferred embodiment of the invention, the salt is the tert-butyl ammonium salt (compound 1) as shown below.

Decreasing TNFR1

The inventors found that a compound of Formula (I) or a pharmaceutically acceptable salt thereof is capable of decreasing sTNF1R in serum or urine in the animal model of Diabetic Nephropathy by administering an effective therapeutic dose as described above. Any decrease in serum or urine sTNFR1 levels will slow the progressions of the disease and improve the renal function. The amount of decrease in sTNFR1 depends on the initial sTNFR1 levels in the subject treated, the effective therapeutic dose and the treatment duration. Thus, in an embodiment of the invention, the sTNFR1 value in serum is decreased to <4.3 ng/ml, preferably, the sTNFR1 value in serum is decreased to <2.9 ng/ml, more preferably, the sTNFR1 value in serum is decreased <1.0 ng/mL.

In a second aspect of the invention, there is provided a method of treatment of a human subject diagnosed with a renal disease, preferably diabetic nephropathy, having an increased risk of developing chronic kidney disease (CKD) or end stage renal disease (ESRD) or both, the method comprising:
1. obtaining a serum or urine sample from a human subject who has normoalbuminuria (NA), microalbuminuria (MA), macroalbuminuria or proteinuria (PT),
2. measuring the level of sTNFR1 in the subject sample (e.g. using a TNFR1 antibody),
3. comparing the subject sample levels of sTNFR1 with reference sample levels of sTNFR1,
4. determining whether the subject has an increased risk of developing CKD or ESRD, or both, based on the comparison of the subject sample levels with the reference levels, wherein the presence of sTNFR1 in the subject serum sample at levels of at least 2.9 ng/ml indicates that the subject has an increased risk of developing CKD, ESRD, or both,
5. administering a therapeutically effective dose of a compound of Formula I to any subjects identified under point 4) as having an increased risk of developing CKD, ESRD or both; and
6. optionally continuing monitoring said identified subjects for a reduction in the level of TNFR1.

EXAMPLES

Methods of Detection of Biomarkers

In the examples below, the sTNFR1 and sTNFR2 were measured using the commercial ELISA kits mouse/rat TNFRI/TNFRII Quantikine ELISA kits from R&D Systems according to the manufacturers protocol. However, for the purpose of measuring the sTNFR1 and sTNFR2 in humans for determining the relevant population groups according the present invention, the method described in Krolewski A. S. *Diabetes Care* 2015; 38:954-962 and Krolewski A. S. et al. *Kidney Int.* 2017 June; 91(6): 1300-1311 should be used.

Example 1—Diabetic Nephropathy Rat Model

Surgical Procedures

The pancreatectomy and uninephrectomy (see below) were conducted during a single surgical procedure (Secher T et al. *Diabetes* 2018 July; 67(Supplement 1)). Animals were operated in a randomized fashion during several consecutive surgical days. After an overnight full-fast with grids installed in the cages, the rats were pancreatectomized and uninephrectomized under isoflurane anesthesia. Pre-operative analgesia, antibiotics and fluid replacement were administered. Rats were not offered any food from one day before to one day after the surgery, From the second day after surgery they were fed ad libitum.

Pancreatectomy (PX)

Figure 4:
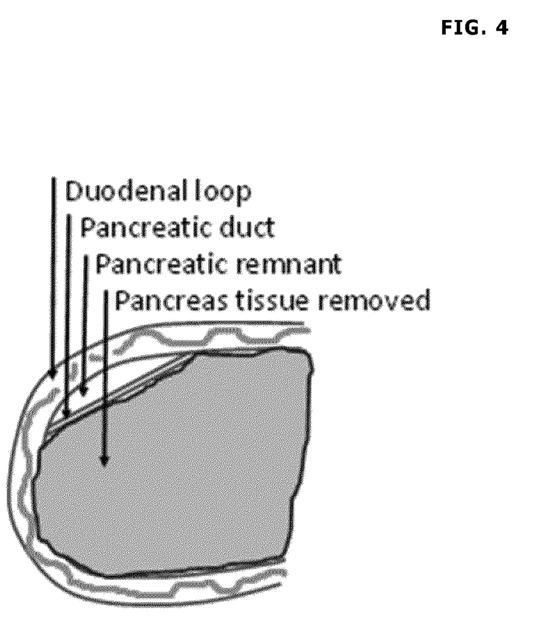
FIG. 4 shows an anatomical map of the pancreas. The remnant (residual pancreas) after 90% pancreatectomy is defined as the white area in FIG. 4.

In short, the 90% pancreatectomy is performed by removing the complete portion of the tail, body and a part of the pancreatic head by gentle abrasion with dental applicator. The major blood vessels to the stomach, spleen and gut are left intact so no other organs are compromised. The remnant (residual pancreas) is defined as the white area according to an anatomical map as shown in FIG. 4.

Uninephrectomy (UNx)

Briefly, the right kidney is visited and the right ureter, kidney artery and kidney vein identified, and ligated with suture. Hereafter, the right kidney is removed.

Sham Operation

The sham operation is conducted to mimic the Px-UNx surgical procedure as best as possible. In brief, anesthesia and analgesia as well as opening and closuring the abdominal cavity are conducted as described above. After the abdominal cavity is opened, the pancreas and right kidney will be exposed, but left untouched and intact.

Urine Sampling

Rats were placed individually in metabolic cages for 16 h from the afternoon to the next morning. Randomized subsets of the study groups were placed in the cages over several days (as there were fewer cages than rats). Rats were supplied with chow and water ad libitum. Cage enrichment (igloo, plastic stick to sit on) was included if possible. Total urine volume was recorded, and urine stored at −80° C. Large amounts were aliquoted in several 0.5 ml Eppendorph tubes prior to freezing.

Urine Assays

Urine samples were stored at −80° C. until analysis. sTNFR1 in rat urine was measured using commercial ELISA kits (R&D Systems mouse/rat TNFRI/TNFRII Quantikine ELISA kits) according to the manufacturer's instructions. Urine creatinine was measured using the CREP2 kit (Roche Diagnostics, Germany) on the Cobas™ C-501 autoanalyzer as per the manufacturer's instructions. Urinary albumin was measured using the Bethyl Laboratories rat albumin ELISA as per the manufacturer's instructions. The urinary albumin-to-creatinine ratio (UACR) was calculated.

Test Plan

Five groups of male Sprague-Dawley rats were included in the study: three surgically treated groups receiving compound 1, one group receiving placebo (vehicle) and one Sham-operated group, also receiving placebo. The groups are summarized in Table 1 below.

TABLE 1

The Sprague-Dawley rats were dosed orally once daily.

| Group | Name | Dose (mg/kg) | Model | Number of rats |
| --- | --- | --- | --- | --- |
| 1 | Sham Vehicle | — | Sham | 12 |
| 2 | Px-Unx Vehicle | — | Px-Unx | 11 |
| 3 | Px-Unx Low | 1 | Px-Unx | 12 |
| 4 | Px-UNx Intermediate | 3 | Px-Unx | 9 |
| 5 | Px-UNx High | 10 | Px-Unx | 12 |

Results

The urine concentrations of sTNFR1 corrected for urine concentration of creatinine (pg/mg) at baseline and 4 and 7 weeks for the individual groups 1-5 were as shown in Table 2:

TABLE 2

| Time | Group 1 (Sham) | Group 2 (Placebo) | Group 3 (1 mg/kg) | Group 4 (3 mg/kg) | Group 5 (10 mg/kg) |
| --- | --- | --- | --- | --- | --- |
| 0 weeks | 35.98 | 259.50 | 243.38 | 236.29 | 220.27 |
| 4 weeks | 23.57 | 426.64 | 373.28 | 313.80 | 348.50 |
| 7 weeks | 21.31 | 446.88 | 345.46 | 369.65 | 375.03 |

Table 2 shows the sTNFR1 values in pg pr. mg creatinine for the groups 1-5 at weeks 0, 4 and 7.

As can be seen from Table 2, the corrected sTNFR1 values for the 3 treatment groups are consistently below the values for the placebo group at both 4 weeks and 7 weeks, indicating a treatment effect of compound 1. However, no statistically significant difference between dosage levels (1, 3 or 10 mg) could be observed at this point. This suggests that full efficacy is already obtained at the lowest dose and hence that even lower doses than 1 mg/kg is enough to lower the sTNFR1 in urine. It was therefore decided to pool the dosage data to arrive at the following set of data shown in Table 3.

TABLE 3

Pooled data from Table 2

| Time | Sham operated (n = 12) | Vehicle (n = 11) | Treated (n = 33) |
| --- | --- | --- | --- |
| 0 weeks | 35.98 | 259.5 | 233.3 |
| 4 weeks | 23.57 | 426.64 | 345.2 |
| 7 weeks | 21.31 | 446.88 | 363.4 |

The data shown in Table 3 was plotted as the change in sTNFR1 concentration vs. baseline values (see FIG. 2). As can be seen from FIG. 2, the Sham-operated rats experience a slight reduction in TNFR1 levels over the 7 weeks of the study, whereas the Px-UNx operated rats receiving placebo (vehicle) display rapidly increasing levels of sTNFR1 over the same period. The compound 1 treated and Px-UNx operated rats also display increasing levels of sTNFR1 over the 7-week period, but significantly less than for the placebo control group. This data demonstrates the effect of compound 1 in decreasing sTNFR1.

Likewise, the urine concentrations of sTNFR2 corrected for urine concentration of creatinine (pg/mg) were measured at baseline and after 4 and 7 weeks in group 3. The data are summarized in Table 4:

TABLE 4

| Time | Group 1 (Sham) | Group 2 (Placebo) | Group 3 (1 mg/kg) |
| --- | --- | --- | --- |
| 0 weeks | 2521 | 5212 | 4561 |
| 4 weeks | 1460 | 3473 | 3302 |
| 7 weeks | 1348 | 2743 | 3264 |

Table 4 shows the TNFR1 values in pg pr. mg creatinine for the group 3 at weeks 0, 4 and 7. The data shown in Table 4 was plotted as the change in TNFR2 concentration vs. baseline values (see FIG. 3). As can be seen from FIG. 3, the change in TNFR2 values for group 3 (treated group) is less pronounced compared to group 2 (placebo). This shows that the sTNFR2 pathway is left intact compared to the placebo group resulting in the beneficial effects of increased tissue regeneration.

Example 2

A clinical Phase 2a study with compound 1 was conducted in patients with diabetic nephropathy. The patients were divided into two different subgroups having either macroalbuminuria (ACR>300 mg/g) or microalbuminuria (ACR 30-300 mg/g), and each subgroup were treated with 0.3 mg of compound 1/kg daily or 0.625 mg of compound 1/kg daily for 4 weeks. No statistic significant difference between the two doses was observed in each subgroup, and the data was pooled. This suggests that full efficacy is already obtained at the lowest dose and hence that even lower doses than 0.3 mg/kg daily are enough to improve ACR. A statistically significant reduction in ACR was observed in both subgroups from baseline. The data are summarized in Table 5 below:

TABLE 5

| Patients | Microalbuminuria (n = 38) | Macroalbuminuria (n = 11) |
|---|---|---|
| Average baseline ACR | 91.8 mg/g | 691 mg/g |
| Average ACR (4 weeks) | 72.6 mg/g | 510 mg/g |
| ACR reduction (%) | 20.9% | 26.2% |

Table 5 shows that the compound 1 was effective in improving ACR in both patient groups. However, the subgroup with macroalbuminuria (ACR >300 mg/g) showed a statistic significant higher reduction in ACR (26.2%) compared to the sub-group with microalbuminuria (ACR 30-300 mg/g) in which the ACR reduction was (20.9%). This observation is in good agreement with the finding that compound 1 is capable of lowering or antagonizing TNFR1 since elevated TNFR1 has previously shown to be correlated with elevated ACR. Thus, in conclusion, compound 1 performed best in the subgroup having macroalbuminuria (ACR>300 mg/g).

Example 3—Synthesis of (Z)-6-(-2-(2-chlorophenyl)-4-(2-hydroxyphenyl)-1,3-dioxan-hex-4-enoic acid Step 1: Synthesis of Racemic 2-methoxy-paraconic Acid as a Cis/Trans Mixture:

A 20 L double-jacketed glass reactor was charged with 260 g o-methoxybenzaldehyde, 286 g succinic anhydride, 572 g anhydrous zinc chloride and 2600 mL anhydrous dichloromethane (DCM). The mixture was stirred and cooled to 2° C. An amount of 533 mL triethylamine was added over a period of 30 min. The mixture was then allowed to stir at ambient temperature for 24 h. An amount of 1690 mL 2M HCl was added, followed by 2600 mL ethyl acetate. The mixture was stirred vigorously for 5 min. The aqueous phase was extracted with 2000 mL ethyl acetate. The combined organic extracts were washed with 650 mL saturated brine, followed by a wash with 3×2600 mL saturated sodium bicarbonate. The combined aqueous extracts were then washed with ethyl acetate. The aqueous extracts were acidified to pH 2 using concentrated HCl. A yellow oil separated. The mixture was extracted twice using 2000 mL ethyl acetate. The organic phase was washed four times with 1000 mL brine and evaporated on a Buchi R220 rotavap employing a heating bath temperature of 45° C. To the remaining residue was added 4000 mL toluene. The mixture was heated to 110° C. 1 L of toluene was distilled off. The remainder was allowed to cool to room temperature and was left standing for 48 h during which pure 2-methoxyparaconic acid crystallized. The crystalline material was collected, filtered and dried in vacuo at 45° C. in a vacuum oven until constant weight.

Yield: 220 g (49%). cis/trans ratio: 46/54.

Step 2: Conversion of Cis- and Trans Racemic Methoxy-Paraconic Acid to all-Trans-2-Methoxy-Paraconic Acid:

1020 g methoxyparaconic acid was added to a mixture of 1729 mL concentrated sulfuric acid and 2570 mL water. The mixture was allowed to stir at room temperature for 18 h. A cis/trans ratio of 33:64 was obtained. The mixture was heated to 60° C. for 2.5 h. A cis/trans ratio of 11:89 was obtained (analysis by HPLC). The mixture was then allowed to cool to room temperature, and subsequently filtered. The solid material was redissolved in ethyl acetate and washed with water and brine. The organic layer was dried over MgSO4 and evaporated. A cis/trans ratio of 6:94 was observed. The solid material was recrystallized from hot toluene. The obtained crystalline material was dried in vacuo at 40° C. for 48 h. Yield: 855 g (84%). cis/trans ratio: 8/92. Melting point: 132-133° C. H-NMR (CDCl3, 300 MHz): 2.9 (2H, d), 3.4 (1H, m), 3.83 (3H, s), 5.85 (1H, d), 6.8-7.4 (4H, m)

Step 3: Esterification of Racemic Methoxy-Paraconic Acid:

193 g of methoxy-paraconic acid was dissolved in 600 mL THF. To the mixture was added 145 g CDI (899 mmol, 1.1 eq), and the mixture was stirred for 10 min. An amount of 65 mL absolute ethanol (or methanol to make the methyl ester) was added, and the mixture was stirred till complete (~120 min). The crude reaction mixture was extracted using ethyl acetate and saturated sodium bicarbonate. The organic phase was washed with 0.5N HCl and brine. After evaporation, an amount of 188 g of the desired ethyl ester were obtained.

Step 4: Reduction of Racemic Methoxy-Paraconic Acid, Ethyl Ester:

Preparation of racemic lactol: To 105 g ethyl ester (397 mmol) in 700 mL toluene at was added 3 eq. DIBAL-H (1.19 mol, 1.19 L 1 M solution). The mixture was stirred for 60 min at room temperature and quenched with methanol. Ethyl acetate (2.5 L) and water (700 mL) were added. After phase separation, the aqueous phase was again extracted with EtOAc. The organic layer was then washed with brine, filtered and evaporated. The oily residue was recrystallized from chloroform/hexanes. The solids were filtered and dried in vacuo. Yield: 53 g (237 mmol, 59%).

Step 5: Wittig Reaction Employing Racemic Lactol-Synthesis of Racemic Diol:

An amount of 191 g carboxypropyltriphenylphosphonium bromide, 1000 mL anhydrous toluene and 100 g potassium t-butoxide were mixed at 80° C. for 30 min. The mixture was cooled to room temperature. An amount of 25 g purified racemic lactol (114.5 mmol) pre-dissolved in 180 mL anhydrous THF was slowly added. The reaction was continued for 60 min. The crude reaction mixture was poured into 1500 mL ice-water, 300 mL ethyl acetate was added. The aqueous phase was re-extracted with 300 mL ethyl acetate. The aqueous phase was then acidified with 2N HCl and extracted 3 times using 300 mL ethyl acetate. The solids that had formed were filtered off. The organic phase was evaporated. To the evaporated residue was added 500 mL diethyl ether. The flask was swirled for 10 min, and the solids were filtered off. The filtrate was extracted 3 times with saturated sodium bicarbonate solution. The aqueous phase was then acidified to pH 4 using 2M HCl. The aqueous phase was then extracted 3 times employing 200 mL of ethyl acetate. The organic phases were combined, dried over MgSO4 and evaporated to yield 45 g of material.

Column Chromatography:

Racemic diol was purified over silica gel (35 cm column length, 4 cm diameter). Racemic diol was dissolved in a minimum of ethyl acetate and applied to the column. 1 L of ethyl acetate (60%)/hexanes (40%) was added to a volumetric cylinder. 300 mL of EtOAc/hexanes was taken from the cylinder and added to the column. The remaining 700 mL of EtOAc/hexanes in the cylinder were diluted to 1 L using ethyl acetate. 300 mL of the new EtOAc/hexanes solution were then added to the column and allowed to pass through the column. The remaining 700 mL of EtOAc/hexanes in the cylinder were again diluted to 1 L using ethyl acetate. 300 mL of the new EtOAc/hexanes solution were then added to the column and allowed to pass through the column. The remaining 700 L of EtOAc/hexanes in the cylinder were diluted once more to 1 L using ethyl acetate. 300 mL of the new EtOAc/hexanes solution were then added to the column and allowed to pass through the column. Pure fractions of racemic diol were collected and evaporated to yield 26 g of pure racemic diol. Yield: 26 g (88.3 mmol, 79%).

Step 6: Conversion of Racemic Diol into Racemic Acetonide:

26 g (88 mmol) of purified diol was mixed with 260 mL dimethoxypropane and 26 mg p-TsOH. The mixture was allowed to stir at ambient temperature overnight. Three drops of triethylamine were added, and the mixture was evaporated. To the remaining residue were added 150 mL hexane, and the mixture was stirred overnight. The solids were filtered off and dried to yield 25 g (75 mmol) of racemic acetonide. Yield: 85%

Step 7: De-Methylation of Racemic Acetonide:

A suspension of sodium hydride and ethanethiol was prepared by adding 16.7 g of ethanethiol to a mixture of 21.5 g NaH in 375 mL DMPU. The suspension was heated to 80° C. and allowed to cool to ambient temperature. 15 g of racemic acetonide was dissolved in 75 mL DMPU and added to the suspension of EtSH/NaH. The mixture was heated at 130° C. for 2 h. The reaction mixture was then poured into ice-water and extracted with DCM. The aqueous layer was acidified using 2N HCl and extracted with ethyl acetate. The organic layer was washed with brine and evaporated to dryness. Yield: 16.5 g (crude).

Step 8: Preparation of Racemic Final Compound:

An amount of 28 mmol de-methylated racemic acetonide was mixed with 15 mL 2-chlorobenzaldehyde, 0.5 g of p-TsOH, and 60 mL of toluene. The mixture was stirred for 24 h and evaporated. The crude reaction mixture was purified using silica gel chromatography employing a Biotage Horizon® chromatography instrument. The mixture was purified using DCM (19)/methanol (1) to yield 6.5 g of a solid after evaporation. Yield: 6.5 g (16.7 mmol, 59%)

Chiral Chromatography

Each enantiomer of the product of STEP 8, i.e. the compounds (Z)-6-((2S,4S,5R)-2-(2-chlorophenyl)-4-(2-hydroxyphenyl)-1,3-dioxan-5-yl)hex-4-enoic acid (enantiomer 1) and (Z)-6-((2R,4R,5S)-2-(2-chlorophenyl)-4-(2-hydroxyphenyl)-1,3-dioxan-5-yl)hex-4-enoic acid (enantiomer 2, as per elution on chiral column below), was isolated by chiral chromatography under the following conditions:

Column: 250×4.6 mm Chiralpak AD-H 5 mm
Mobile phase: 80/20/0.1 n-Heptane/Ethanol/Trifluoroacetic acid
Flow rate: 1 ml/min
Detection: UV at 230 nm
Temperature: 25° C.

Samples were dissolved in 80/20 n-Heptane/Ethanol. Enantiomer 1 elutes first on the chiral column and Enantiomer 2 eluted second on the chiral column.

Conversion to Salt

The enantiopure (enantiomer 1) acid (452.23 mg, 1.12 mmol) obtained above was dissolved in IPA (2 mL) at room temperature. The solution was heated to 50° C. and t-butylamine added. A crystalline material precipitated after 1 hour. The volume of IPA was increased to 23 mL and the material redissolved with heating and cooled to room temperature over 48 hours. A crystalline white material was obtained in 34% yield. Characterization of this material identified it as an IPA solvate with a chemical purity of 95.4%. Diffractometry shows the formation of the t-butylammonium salt of the compound as an IPA solvate.

The invention claimed is:

1. A method for the treatment of a population of patients suffering from a renal disease, wherein the population to be treated is characterized by having a serum level of sTNFR1 of >2.9 ng/ml and/or an ACR>300 mg/g, and wherein said method comprises administering a therapeutically effective amount of a compound of formula (I)

formula (I)

2. The method according to claim 1, wherein the renal disease is diabetic nephropathy.

3. The method according to claim 1, wherein the elevated sTNFR1>4.3 ng/mL.

4. The method according to claim 1, wherein the compound is administered as a daily dose in the range of 0.16 mg/kg to 1.6 mg/kg.

5. The method according to claim 1, wherein sTNF1R and/or ACR in serum or urine in a subject is decreased.

6. The method according to claim 1, wherein the sTNFR1 value in serum or urine is decreased to <4.3 ng/mL.

7. The method according to claim 1, wherein the compound is administered as a daily dose of 0.3 mg/kg daily.

8. The method according to claim 1, wherein the compound is administered as a daily dose of 0.625 mg/kg daily.

9. The method according to claim 1, wherein the sTNFR1 value in serum or urine is decreased to <2.9 ng/mL.

* * * * *